(12) United States Patent
Günther et al.

(10) Patent No.: US 6,258,933 B1
(45) Date of Patent: Jul. 10, 2001

(54) PROCESS FOR THE ONE-STAGE RESALTING AND PURIFICATION OF OLIGOPEPTIDES

(75) Inventors: Kurt Günther; Franz-Rudolf Kunz; Karlheinz Drauz; Thomas Müller, all of Staatsangehorigkeit (DE)

(73) Assignee: Degussa-Huls Aktiengesellschaft (DE)

(*) Notice: Subject to any disclaimer, the term of this patent is extended or adjusted under 35 U.S.C. 154(b) by 0 days.

(21) Appl. No.: 09/276,709

(22) Filed: Mar. 26, 1999

(30) Foreign Application Priority Data

Mar. 27, 1998 (DE) .............................. 198 13 849

(51) Int. Cl.$^7$ ...................................... C07K 1/16
(52) U.S. Cl. .................... 530/344; 530/345; 530/412; 530/416; 530/417
(58) Field of Search ................................ 530/344, 345, 530/412, 416, 417

(56) References Cited

U.S. PATENT DOCUMENTS 4,018,912 * 4/1977 Failli .................................... 424/177

FOREIGN PATENT DOCUMENTS 2 152 059    7/1985 (GB).

OTHER PUBLICATIONS

Chemical Abstracts, vol. 112, No. 23, Jun. 4, 1990 Columbus, Ohio, US; Abstract No. 217553, J. Michalsky, et al., "Preparation of Alpha–aspartylphenylalanine Methyl and Ethyl Esters", XP002109980 & CS 261262 A (Michalsky, et al).

Chemical Abstracts, vol. 118, No. 11, Mar. 15, 1993 Columbus, Ohio, US; Abstract No. 102429, H. Naharissoa, et al, "Use of 6M Hydrochloric Acid for Removal of the N–alpha–tert–butyloxycarbonyl Group During Solid–phase Peptide Synthesis", XP002109981 & Pept Res, Bd. 5, Nr. 5, 1992, pp. 293–299.

Chemical Abstracts, vol. 111, No. 25, Dec. 18, 1989 Columbus, Ohio, US; Abstract No. 233550, Y. Kawasaki, et al., "Development for the Simple Synthetic Method of Oligopeptides", XP002109982 & Chem. Express, Bd. 3, Nr. 11, 1988, pp. 703–706.

* cited by examiner

Primary Examiner—Christopher S. F. Low
(74) Attorney, Agent, or Firm—Pillsbury Madison & Sutro LLP

(57) ABSTRACT

The present invention relates to a process for the one-stage resalting and purification of oligopeptides. Oligopeptides are often not formed directly as acetates when synthesised. Acetate salts of oligopeptides are however desirable as bulk-active material for medical and formulation reasons. Processes known from the prior art have hitherto involved two separate steps or pyridine-containing solvents. The resalting and purification can be combined in one step and the use of pyridine as solvent can be avoided, if the oligopeptide in the form of its chloride salt is purified with an acetate-containing solvent by liquid chromatography methods.

16 Claims, 5 Drawing Sheets

PROCESS FOR THE ONE-STAGE RESALTING AND PURIFICATION OF OLIGOPEPTIDES

CROSS-REFERENCE TO RELATED APPLICATION

This application claims priority from German Application No. 19813849.0, filed on Mar. 27, 1998, the complete disclosure of which is incorporated herein by reference.

BACKGROUND OF THE INVENTION

1. Field of the Invention

The present invention relates to a one-stage process for the resalting and purification of oligopeptides.

2. Background Information

Oligopeptides frequently display biological activity and are therefore used as therapeutic agents. LHRH agonists and antagonists may be mentioned by way of example, which are used, inter alia, to treat certain types of cancer.

The oligopeptides to be purified may be prepared according to processes known in the prior art. Suitable processes include, among others, the Merrifield peptide synthesis on solid support materials or the conventional synthesis in solution. Both in the Merrifield solid phase synthesis and in synthesis in solution it is essential to provide certain regions in the molecule with protective groups that are split off at the end of the preparation. In the solid phase synthesis it is moreover necessary to remove the oligopeptide from the solid support. For further details of the synthesis of peptides reference may be made to the relevant literature (Houben-Weyl, Methoden der organischen Chemie, Vol. 15/1 and 15/2; M. Bodanszky, Principles of Peptide Synthesis, Springer Verlag 1984).

If the peptide to be prepared is a pharmaceutical, then it is often desirable for the oligopeptide to be present in the form of its acetate salt in order not to have to give the patient any foreign or other potentially harmful substances in conjunction with the administration of the drug.

It is often the case, however, that the oligopeptide, owing to circumstances connected with the synthesis, does not necessarily exist in the form of the acetate salt, either because acids other than acetic acid have to be used for the final cleavage of the protective groups, or because the free form of the peptide cannot be prepared or can be prepared only with difficulty and it is not possible to perform a simple conversion to the acetate by means of acetic acid. In order to cleave the protective groups or to cleave the peptide from the resin required for the synthesis, recourse generally has to be made to relatively strong acids such as trifluoroacetic acid, hydrochloric acid or hydrobromic acid. For further details of these cleavage processes reference may be made once again to the standard textbooks (Houben-Weyl, Methoden der organischen Chemie, Band 15/1 and 15/2; M. Bodanszky, Principles of Peptide Synthesis, Springer Verlag 1984).

In order to prepare the required acetate of the relevant oligopeptide for use in animals or humans, one is required in the aforementioned cases to resalt the oligopeptide.

The oligopeptide to be tested as active substance, or that is already available commercially as a therapeutic agent, must satisfy particular requirements as regards its purity. Because of the lack of a suitable conventional purification method, the product mixture formed in the synthesis is generally purified by means of chromatography, in particular high pressure liquid chromatography. For this purpose the oligopeptide must be taken up in a solvent, preferably in the solvent mixture of the mobile solvent chosen as eluent, before it is applied to the column.

For oligopeptides several processes have previously been described in the literature that relate to their resalting and purification. According to Gabriel (Int. J. Peptide Protein Res. 1987, 30, 40–43) the oligopeptide GRF (1–44) —$NH_2$ can be converted from its trifluoroacetate into the acetate by means of high pressure liquid chromatography using pyridine-containing and acetic acid-containing solvents. With regard to the pyridine residues that inevitably remain in the oligopeptide after such a procedure, there is concern, of course, about the toxicological properties of this substance. Also, a purification process that involves relatively large amounts of dangerous pyridine is undesirable from industrial safety aspects.

Hoeger et al. (Biochromatography 1987, 2, 134–142) have attempted to resalt and purify GnRH peptides while avoiding the use of a pyridine-containing solvent system. Starting from the fluoride salts, a two-stage reversed phase gradient chromatography was carried out in triethylammonium phosphate (TEAP) and trifluoroacetate (TFA) buffers with acetonitrile as modifier. Lyophilisation of the purified peptide fractions was followed by conversion to the acetate salts via anion exchange chromatography with dilute acetic acid or reversed phase chromatography in an ammonium acetate/acetonitrile gradient.

EP 0145258 describes, inter alia, the purification of HF salts of nonapeptides and decapeptides of the group of LHRH agonists. Here, too, the resalting takes place separately from the purification step, first via anion exchange chromatography followed by final purification on an octadecyl-silanised silicic gel phase by means of an eluent consisting of ammonium acetate and acetonitrile under high pressure conditions.

SUMMARY OF THE INVENTION

The object of the present invention is to provide a further process for the resalting and purification of oligopeptides that combines these two operational steps in one step and avoids the use of pyridine.

This and other objects, which are not identified more precisely but which however are obvious from the prior art to the person skilled in the art, are the subject of the characterising part of claim 1. Prefered modifications of the process according to the invention are the subject of the subclaims dependent on claim 1.

By purifying the oligopeptide, in the form of its hydrochloride salt, that is to be resalted and purified, via liquid chromatography by means of an acetate-containing solvent, practically chloride-free purified oligopeptide acetates are obtained in an extremely simple but nevertheless advantageous manner. It is thus possible with the process according to the invention to combine the effective purification and resalting of the oligopeptides in question, which hitherto could only be achieved in two stages or by using toxicologically harmful pyridine, in one single operational step without the addition of pyridine. The product fractions obtained by the present process are advantageously combined and dried by lyophilisation. The acetate is obtained in a yield of ca. 85% from the chloride. The pure oligopeptide acetate that is thus obtained in a percentage of up to 99.5% can after appropriate formulation be used as an active agent for medical treatment and therapy.

For the present process the oligopeptides must be used in the form of their chlorides. The simplest way to achieve this is to use hydrochloric acid for the protective group cleavage. On the other hand, the peptide hydrolysis and other secondary reactions occurring at side-chain groups as a result of the acid strength of the cleavage agent constitute undesirable competition reactions. For these and other reasons (for example the solubility of the peptide in TFA) weaker anhydrous acids such as trifluoroacetic acid or anhydrous strong acid mixtures such as HBr/acetic acid are often used for such protective group cleavages.

It has now completely surprisingly but nevertheless advantageously been found that protected oligopeptides can also be de-protected with concentrated aqueous hydrochloric acid and that the salts of the oligopeptides formed therefrom contain a significantly lower proportion of by-products compared to the more conventional cleavage with the less strong, anhydrous trifluoroacetic acid, possibly mixed with organic solvents, or with the HBr/acetic acid system. This was neither obvious nor forseeable.

The aforedescribed cleavage of the protective groups from the oligopeptide is preferably carried out in a temperature range from −25° C. to 30° C., more preferably from −10° to 10° C., and even more preferably from 0° to 5° C.

The chloride salt of the oligopeptide may be used in the form of its concentrated hydrochloric acid aqueous solution for the purification by means of liquid chromatography. It is preferred, however, to isolate the chloride salt, for example by lyophilisation, after cleavage of the protective groups and then first dissolve it in the liquid chromatography solvent system or in acetic acid before adding it to the column.

High pressure liquid chromatography is preferably used as the liquid chromatography method for purifying the oligopeptides. Solvents of the following composition are used as solvent system for the gradient elution:

|   | Solvent A |   | Solvent B |
|---|-----------|---|-----------|
| i. | 85 to 98% water | i. | 20 to 48% water |
| ii. | 2 to 10% acetic acid | i. | 2 to 10% acetic acid |
| iii. | 0 to 5% acetonitrile | iii. | 50 to 70% acetonitrile | or

|   | Solvent A |   | Solvent B |
|---|-----------|---|-----------|
| i. | 85 to 98% water | i. | 0 to 10% water |
| ii. | 2 to 10% acetic acid | ii. | 2 to 10% acetic acid |
| iii. | 0 to 5% methanol | iii. | 80 to 98% methanol |

For the gradient elution there is preferably used a solvent mixture comprising

|   | Solvent A |   | Solvent B |
|---|-----------|---|-----------|
| i. | 92% water | i. | 28% water |
| ii. | 5% acetic acid | ii. | 5% acetic acid |
| iii. | 3% acetonitrile | iii. | 67% acetonitrile | or

|   | Solvent A |   | Solvent B |
|---|-----------|---|-----------|
| i. | 90% water | i. | 5% water |
| ii. | 5% acetic acid | ii. | 5% acetic acid |
| iii. | 5% acetonitrile | iii. | 90% acetonitrile |

The purification is preferably carried out at a column temperature from 5° to 50° C., more preferably from 15° to 35° C., and most preferably from 20° to 30° C. The column pressure should be between 5 and 100 bar, preferably between 20 and 80 bar, and more preferably between 30 and 60 bar. In principle all materials known to the person skilled in the art may be used as stationary phase for the purification. A reversed phase material is particularly suitable. The expression reversed phase material is understood to mean column packings that are based on support materials such as silica gel or organic polymers. In the case of silica gels the hydrophilic surfaces may be modified by organosilanes. For this purpose C-2, C-8 or C-18 modifications, among others, are suitable. It is more preferred to use a C-18-modified RP-18 phase, and most preferred to use Nucleosil® 300-7-$C_{18}$ from Macherey & Nagel or Purospher® RP 18 (10 μm) from Merck.

Oligopeptides within the context of the present application are understood to mean peptides with five to twenty-five amino acids. The range of oligopeptides with eight to twelve amino acids is preferred. It is more preferred to use oligopeptides with 10 amino acids.

The aforedescribed liquid chromatography method for resalting and purifying the oligopeptides can be carried out according to the so-called simulated moving bed technique as well as by means of cyclic chromatography.

The process according to the invention is particularly advantageously used in a synthesis for preparing the LHRH antagonists Cetrorelix (1) and Antarelix (2)

Ac-D-Nal(2)-D-Phe(4Cl)-D-Pal(3)-Ser-Tyr-D-Cit-Leu-Arg-Pro-D-Ala-NH$_2$·2CH$_3$COOH     1

Ac-D-Nal(2)-D-Phe(4Cl)-D-Pal(3)-Ser-Tyr-D-Hci-Leu-Lys(ε-iso-propyl)-Pro-D-Ala-NH$_2$·2CH$_3$COOH     2

The introduction of tert.-butyl protective groups in the side chain of serine and tyrosine has proved particularly suitable in the synthesis. In order to obtain the end product these protective groups must be split off again under acid conditions (TFA or HCl). In the cleavage of the tert.-butyl groups with hydrochloric acid significantly fewer by-products are formed than when using TFA. The optimized separation process is suitable for the process chromatography and permits the use of preparative HPLC columns having internal diameters of more than 30 cm and injection amounts of more than 200 g per chromatography run.

Owing to the process according to the invention the aforementioned oligopeptides can for example be prepared in a more advantageous and thus economically more favorable manner on a multikilogram scale.

The starting substances for the invention described herein can be prepared by methods known per se to the person skilled in the art. Reference may be made to the relevant textbooks (Houben-Weyl, Methoden der organischen Chemie, Vol. 15/1 and 15/2; M. Bodanszky, Principles of Peptide Synthesis, Springer Verlag 1984).

DETAILED DESCRIPTION OF THE INVENTION

The following examples are intended to illustrate the invention without however restricting the latter in any way:

EXAMPLE 1

Preparation of Ac-D-Nal-D-p-Cl-Phe-D-Pal-Ser-Tyr-D-Cit-Leu-Arg-Pro-D-Ala-$NH_2 \times 2HCl$ (1a) (Cetrorelix hydrochloride)

Figure 6:
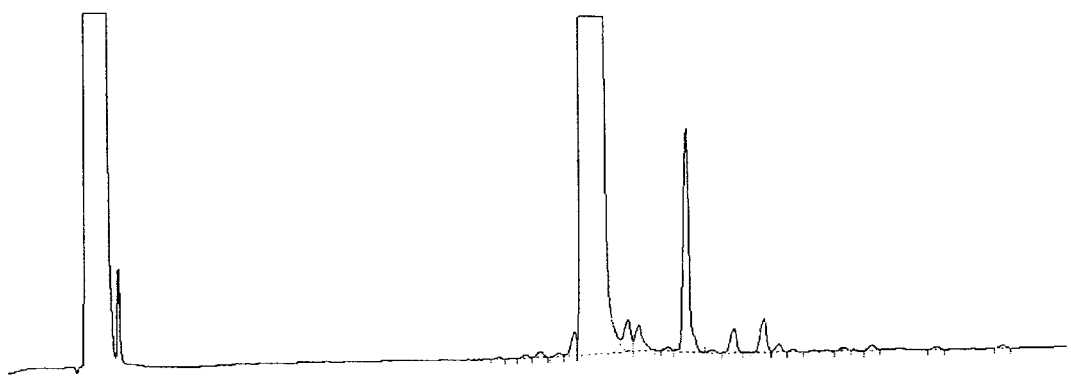
FIG. 6 shows the HPLC analysis of Cetrorelix hydrochloride (Example 1).

50 g (31.65 mmole) of Ac-D-Nal-D-p-Cl-Phe-D-Pal-Ser($^t$Bu)-Tyr($^t$Bu)-D-Cit-Leu-Arg(HCl)-Pro-D-Ala-$NH_2$ is added while stirring vigorously to 200 ml of ice-cold concentrated hydrochloric acid. The reaction mixture is stirred for ca. 1 hour at 0°–5° C., added to a stirred mixture of 0.75 l of n-butanol and 0.5 kg of ice, the phases are separated after adding 120 ml of water, the pH of the organic phase is adjusted to ca. 2 with sodium hydroxide, and the butanolic solution is evaporated in vacuo. The residue is suspended in 0.5 l of tert.-butyl methyl ether, suction filtered, washed with 0.5 l of tert.-butyl methyl ether, and dried in vacuo. Yield of 1a: 49 g (103%, substance contains ca. 4 wt. % NaCl), HPLC purity 94.4 area %. (see FIG. 6).

EXAMPLE 2

Preparation of Ac-D-Nal-D-p-Cl-Phe-D-Pal-Ser-Tyr-D-Cit-Leu-Arg-Pro-D-Ala-$NH_2 \times 2TFA$ (1b) (Cetrorelix trifluoroacetate)

Figure 7:
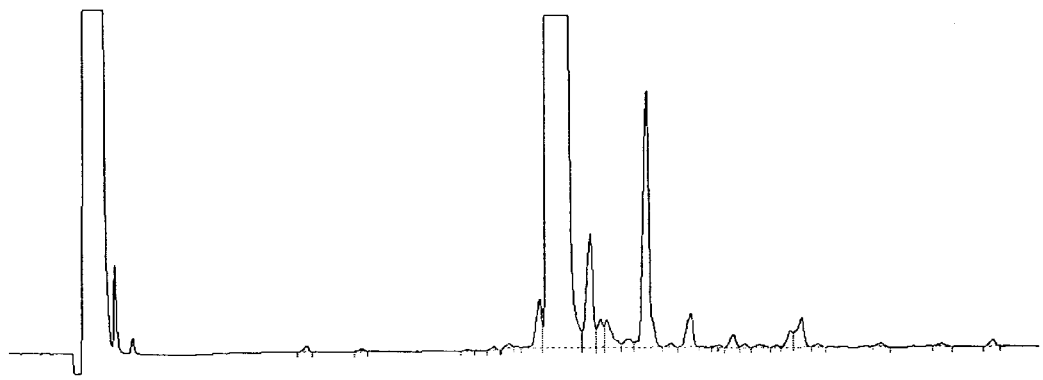
FIG. 7 shows the HPLC analysis of Cetrorelix trifluoroacetate (Example 2).

1 g (0.633 mmole) of Ac-D-Nal-D-p-Cl-Phe-D-Pal-Ser($^t$Bu)-Tyr($^t$Bu)-D-Cit-Leu-Arg(HCl)-Pro-D-Ala-$NH_2$ is dissolved in 10 ml of trifluoroacetic acid, the solution is stirred for 1.5 hours, and is then added to 100 ml of ice-cold diisopropyl ether. The product 1b is suction filtered, washed with diisopropyl ether, and dried in vacuo. Yield of 1b: 1.05 g (100%), HPLC purity 89.6 area %. (see FIG. 7).

EXAMPLE 3

Preparation of Ac-D-Nal-D-p-Cl-Phe-D-Pal-Ser-Tyr-D-Hci-Leu-Lys($\epsilon$-isopropyl)-Pro-D-Ala-$NH_2 \times 2HCl$ (2a) (Antarelix hydrochloride)

Figure 8:
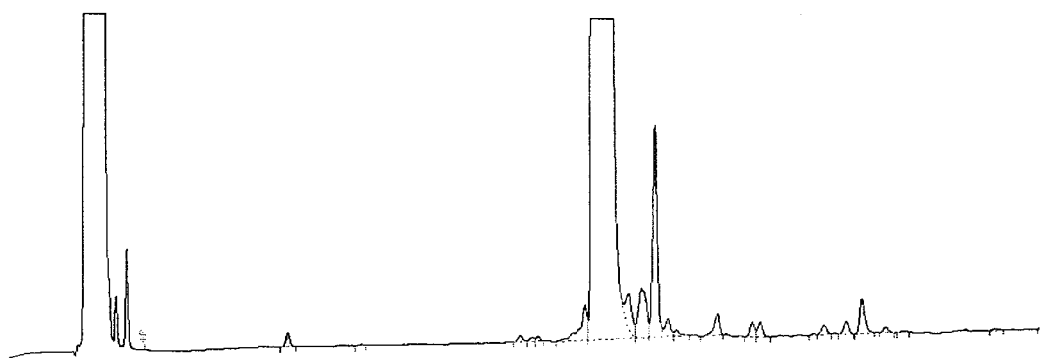
FIG. 8 shows the HPLC analysis of Antarelix hydrochloride (Example 3).

77.3 g (46.2 mmole) of Ac-D-Nal-D-p-Cl-Phe-D-Pal-Ser($^t$Bu)-Tyr($^t$Bu)-D-Hci-Leu-Lys($\epsilon$-Boc) ($\epsilon$-isopropyl)-Pro-D-Ala-$NH_2$ are added while stirring vigorously to 400 ml of ice-cold, concentrated hydrochloric acid. After ca. 1 hour the reaction mixture is poured into a mixture of 0.85 l of water and 0.85 kg of ice, the aqueous solution is extracted twice with in each case 0.9 l of n-butanol, the pH of the combined butanol phases is adjusted to ca. 2 with saturated, aqueous sodium hydrogen carbonate solution, the phases are separated, and the organic phase is evaporated in vacuo. The residue is digested with 2 l of tert.-butyl methyl ether, suction filtered, washed with tert.-butyl methyl ether, and dried in vacuo. Yield 72 g (104%, substance contains ca. 2 wt. % NaCl and remainder butanol), HPLC purity 94.0%. (see FIG. 8)

EXAMPLE 4

Preparation of Ac-D-Nal-D-p-Cl-Phe-D-Pal-Ser-Tyr-D-Hci-Leu-Lys ($\epsilon$-isopropyl)-Pro-D-Ala-$NH_2 \times 2TFA$ (2b) (Antarelix trifluoroacetate)

Figure 9:
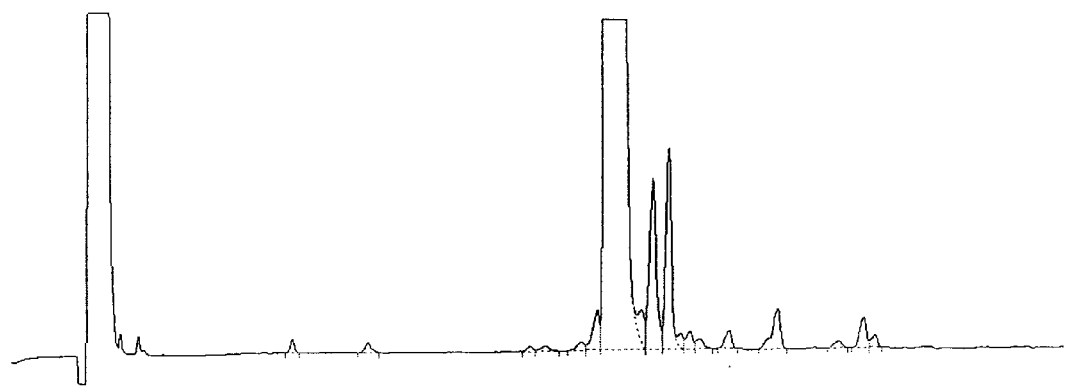
FIG. 9 shows the HPLC analysis of Antarelix trifluoroacetate (Example 4).

1 g (0.6 mmole) of Ac-D-Nal-D-p-Cl-Phe-D-Pal-Ser($^t$Bu)-Tyr ($^t$Bu)-D-Hci-Leu-Lys($\epsilon$-Boc) ($\epsilon$-isopropyl)-Pro-D-Ala-$NH_2$ is dissolved in 10 ml of trifluoroacetic acid, the solution is stirred for about 1.5 hours and is then added to 100 ml of ice-cold diisopropyl ether. The product 1b is suction filtered, washed with diisopropyl ether and dried in vacuo. Yield of 1b : 1.01 g (100%), HPLC purity 89.4 area %. (see FIG. 9)

EXAMPLE 5

Preparative purification of Cetrorelix from the crude product of the conventional synthesis in solution (Example 1):

18 g of the crude product from a process of Example 1 is dissolved in 500 ml of 30% acetic acid and, after filtration (through a Seitz K-700 filter) are applied to the column (length 250 mm, internal diameter 100 mm). Nucleosil 300-7-$C_{18}$ from Macherey & Nagel or alternatively Purospher RP 18 (10 mm) from Merck may be used as stationary phase. The column is first conditioned for 20 minutes with a solvent mixture of 95% mobile phase A (970 ml superpure water+30 ml acetonitrile+50 ml 100% acetic acid) and 5% mobile phase B (700 ml acetonitrile+300 ml superpure water+50 ml 100% acetic acid). Chromatography is then carried out on the Nucleosil phase according to the following gradient program:

| Time (min) | Concentration A (Vol %) | Concentration B (Vol %) |
| --- | --- | --- |
| 0 | 95 | 5 |
| 9 | 95 | 5 |
| 10 | 77 | 23 |
| 22 | 77 | 23 |
| 37 | 67 | 33 |
| 47 | 0 | 100 |
| 55 | 0 | 100 |

The eluent flow is 200 ml/min, a column pressure of 38–60 bar being built up in each case depending on the gradient conditions.

Alternatively, the chromatography is carried out on the Purospher support according to the following gradient programme:

| Time (min) | Concentration A (Vol %) | Concentration B (Vol %) |
| --- | --- | --- |
| 0 | 95 | 5 |
| 20 | 95 | 5 |
| 21 | 70 | 30 |
| 60 | 65 | 35 |

-continued

| Time (min) | Concentration A (Vol %) | Concentration B (Vol %) |
|---|---|---|
| 61 | 0 | 100 |
| 70 | 0 | 100 |

The eluent flow is in this case 300 ml/min, a column pressure of 35–50 bar being built up in each case depending on the gradient conditions.

The peak detection takes place in UV light at 270 nm, a manual fractionation being performed. Rising and falling edges (purity ca. 95%) are observed separated from the main peak (purity>99.5%), which are recycled. Acetonitrile is removed down to a level of ca. 1% from the fractions on a rotary evaporator at ca. 50° C. under a water jet vacuum. The concentrated eluates are then lyophilised.

Figure 1:
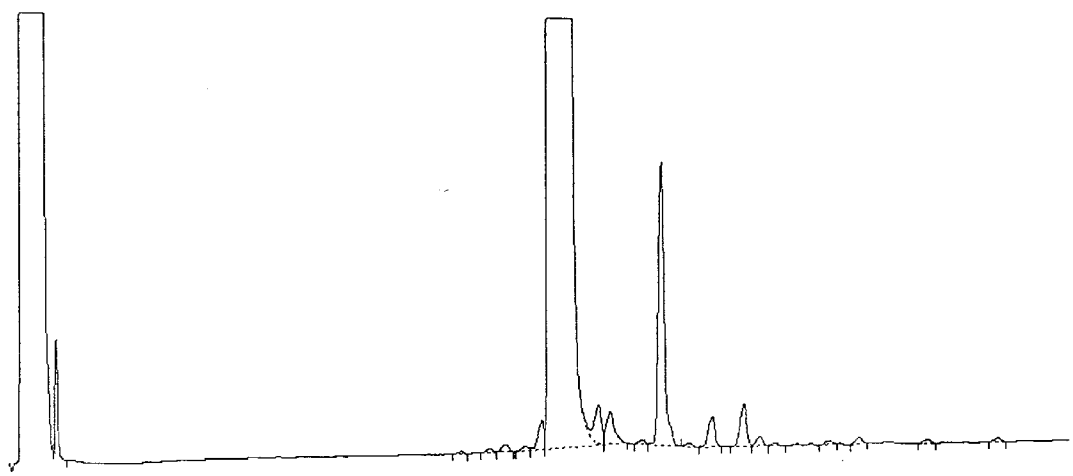
FIG. 1 shows the HPLC analysis of the crude product used.
Figure 2:
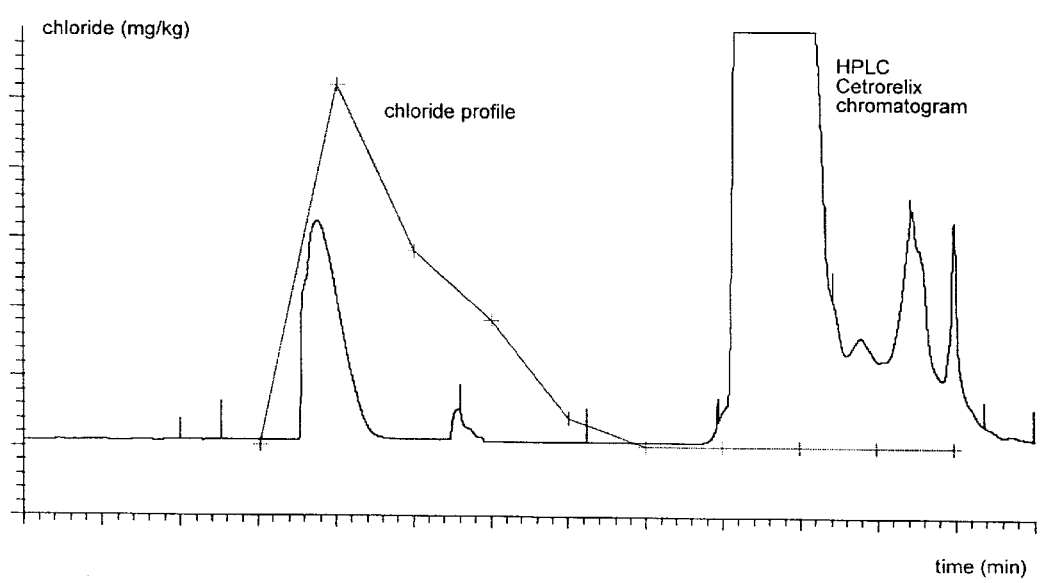
FIG. 2 shows preparative HPLC of the Cetrorelix synthesis crude product on the Nucleosil phase.
Figure 3:
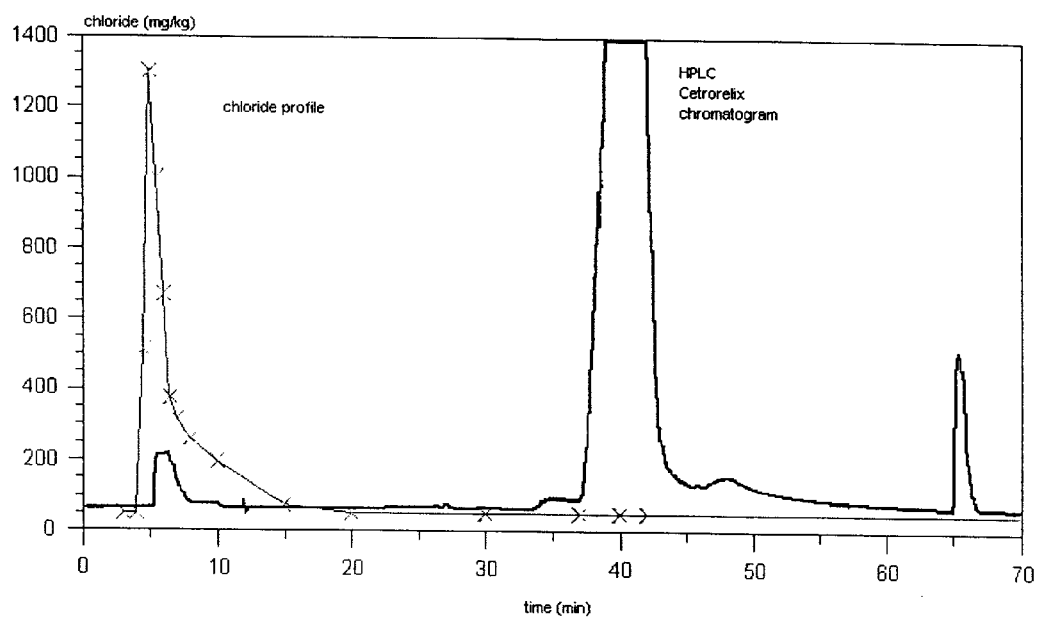
FIG. 3 shows preparative HPLC of the Cetrorelix synthesis crude product on the Purospher support.
Figure 4:
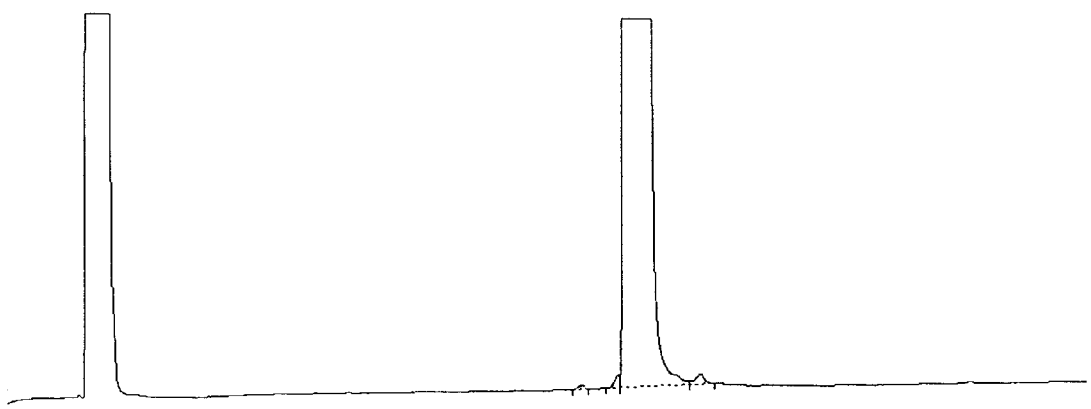
FIG. 4 shows HPLC chromatogram of the purified end product.

HPLC analysis of the crude product used:
    Shown in FIG. 1.
Specification of the crude product:
    Peptide purity: 94.4 area %
    Chloride content: 6.2%
Preparative HPLC of the Cetrorelix synthesis crude product on the Nucleosil phase:
    Shown in FIG. 2.
Preparative HPLC of the Cetrorelix synthesis crude product on the Purospher support:
    Shown in FIG. 3.
HPLC chromatogram of the purified end product:
    Shown in FIG. 4.
Specification of the end product
    Peptide purity: 99.75%
    Chloride content: 220 ppm
    Acetate content: 6.5%

EXAMPLE 6

Preparative purification of Antarelix from the crude product of the conventional synthesis in solution 15 g of the crude product is dissolved in 500 ml of 30% acetic acid and after filtration (through a Seitz K-700 filter), are applied to the column (length 250 mm, internal diameter 100 mm). Purospher RP 18 (10 mm) from Merck serves as stationary phase. The column is first conditioned for 20 minutes with a solvent mixture of 95% mobile phase A (970 ml superpure water+30 ml acetonitrile+50 ml 100% acetic acid) and 5% mobile phase B (700 ml acetonitrile+300 ml superpure water+50 ml 100% acetic acid). Chromatography is then carried out according to the following gradient programme:

| Time (min) | Concentration A (Vol %) | Concentration B (Vol %) |
|---|---|---|
| 0 | 95 | 5 |
| 15 | 95 | 5 |
| 16 | 70 | 30 |
| 56 | 65 | 35 |
| 57 | 0 | 100 |
| 65 | 0 | 100 |

The eluent flow is 300 ml/min, a column pressure of 35–50 bar being built up in each case depending on the gradient conditions. The peak detection is performed in UV light at 270 nm, a manual fractionation being carried out. Rising and falling edges (purity ca. 95%) are detected separated from the main peak (purity>99.5%), which are recycled. Acetonitrile is removed down to a level of ca. 1% from the fractions on a rotary evaporator at ca. 50° C. under a water jet vacuum. The concentrated eluates are then lyophilised.

Figure 5:
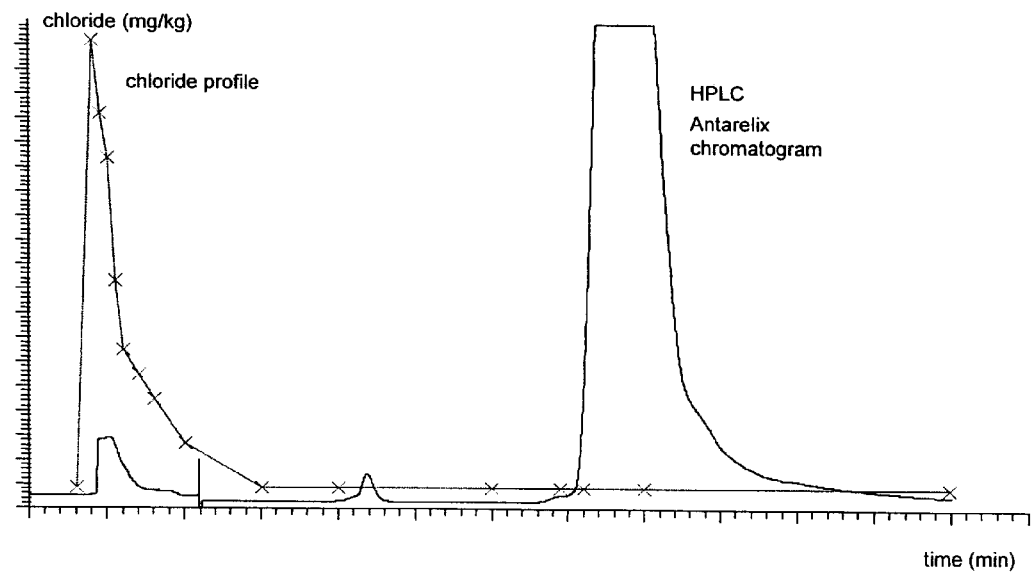
FIG. 5 shows preparative HPLC of the Antarelix synthesis crude product on the Purospher support.

Preparative HPLC of the Antarelix synthesis crude product on the Purospher support:
    Shown in FIG. 5.
Specification of the end product:
    Peptide purity: 99.39%
    Chloride content: <200 ppm
    Acetate content: 7.5%

EXAMPLE 7

Preparative purification of Cetrorelix in the methanol/water/acetic acid system 4 g of the crude product is dissolved in 60 ml of 30% acetic acid and, after filtration (through a Seitz K-700 filter) is applied to the column (length 250 mm, internal diameter 40 mm). Deltapak 300 Å, 15 mm, from Millipore serves as stationary phase. The column is first conditioned for 20 minutes with mobile phase A (950 ml superpure water+50 ml methanol+60 ml 100% acetic acid). Chromatography is then carried out according to the following gradient program (mobile phase B: 950 ml methanol+50 ml superpure water+60 ml 100% acetic acid):

| Time (min) | Concentration A (Vol %) | Concentration B (Vol %) |
|---|---|---|
| 0 | 100 | 0 |
| 10 | 100 | 0 |
| 11 | 70 | 30 |
| 40 | 30 | 70 |
| 41 | 0 | 100 |
| 50 | 0 | 100 |

The eluent flow is 60 ml/min, a column pressure of 20–30 bar being built up in each case depending on the gradient conditions. The peak detection is performed in UV light at 270 nm, a manual fractionation being carried out. Rising and falling edges (purity ca. 95%) are detected separated from the main peak (purity>99.5%), which are recycled. Methanol is removed down to a level of ca. 1% from the fractions on a rotary evaporator at 50° C. and under a water jet vacuum. The concentrated eluates are then lyophilised.

Specification of the end product
    Peptide purity: 99.60%
    Chloride content: 220 ppm
    Acetate content 7.1%

The foregoing is meant to illustrate, but not to limit, the scope of the invention. Those of ordinary skill in the art will be able to readily envision and produce further embodiments, based on the teachings herein, without undue experimentation. References cited herein are hereby incorporated by reference.

What is claimed is:

1. A process for one-stage resalting and purification of an oligopeptide comprising the steps of:
    (a) subjecting the hydrochloride salt of said oligopeptide, dissolved in a suitable solvent, to liquid chromatography with acetic acid-containing solvents; and
    (b) obtaining the acetate salt of the oligopeptide.

2. The process according to claim 1, wherein the step (a), the oligopeptide is dissolved in concentrated hydrochloric acid.

3. The process according to claim 1, further comprising lyophilizing the hydrochloric acid solution of step (a) to obtain a pure hydrochloride salt of said deprotected oligopeptide.

4. The process according to claim 1, wherein the liquid chromatography is high pressure liquid chromatography.

5. The process according to claim 4, wherein solvent A is employed as the initial eluent, and thereafter the oligopeptide is eluted using a mixture of solvent A and solvent B, with the ratio of solvent B to solvent A being increased over time, and where in said process the composition of solvents A and B are as follows:

|      | Solvent A          |      | Solvent B           |
| ---- | ------------------ | ---- | ------------------- |
| i)   | 85 to 98% water    | i)   | 20 to 48% water     |
| ii)  | 2 to 10% acetic acid | ii)  | 2 to 10% acetic acid |
| iii) | 0 to 5% acetonitrile | iii) | 50 to 70% acetonitrile | or

|      | Solvent A          |      | Solvent B           |
| ---- | ------------------ | ---- | ------------------- |
| i)   | 85 to 98% water    | i)   | 0 to 10% water      |
| ii)  | 2 to 10% acetic acid | ii)  | 2 to 10% acetic acid |
| iii) | 0 to 5% methanol   | iii) | 80 to 98% methanol  |

6. The process according to claim 5, wherein the composition of solvents A and B are as follows:

|      | Solvent A       |      | Solvent B       |
| ---- | --------------- | ---- | --------------- |
| i)   | 92% water       | i)   | 28% water       |
| ii)  | 5% acetic acid  | ii)  | 5% acetic acid  |
| iii) | 3% acetonitrile | iii) | 67% acetonitrile | or

|      | Solvent A       |      | Solvent B        |
| ---- | --------------- | ---- | ---------------- |
| i)   | 90% water       | i)   | 5% water         |
| ii)  | 5% acetic acid  | ii)  | 5% acetic acid   |
| iii) | 5% acetonitrile | iii) | 90% acetonitrile. |

7. The process according to one of claims 5 or 6, wherein the process is carried out at a temperature from 5° to 50° C.

8. The process according to one of claims 5 or 6, wherein the process is carried out at a pressure of 5 to 100 bar.

9. The process according to one of claims 5 or 6, wherein reversed phase column material is used as stationary phase.

10. The process according to claim 1, wherein an oligopeptide of at least five and at most twenty-five amino acids is used.

11. The process according to claim 10, wherein a peptide of eight to sixteen amino acids is used.

12. The process according to claim 11, wherein a peptide of ten amino acids is used.

13. The process according to claim 1, wherein the liquid chromatography is carried out according to the simulated moving bed method or by means of cyclical chromatography.

14. A process for resalting and purification of an oligopeptide comprising the steps of:

(a) treating a protected oligopeptide with concentrated hydrochloric acid for a time sufficient to remove the protecting groups and form the hydrochloric salt of the deprotected oligopeptide;

(b) subjecting a solution of the deprotected oligpeptide of step (a), dissolved in a suitable solvent, to liquid chromatography with acetic acid-containing solvents; and (c) obtaining the acetate salt of the oligopeptide.

15. The process according to claim 14, further comprising lyophilizing the hydrochloric acid solution of step (a) to obtain a pure hydrochloric salt of said deprotected oligopeptide.

16. The process according to claim 14, wherein the process is carried out at a temperature of −25° to 30° C.

* * * * *